US00PP33930P2

(12) United States Plant Patent
Probst

(10) Patent No.: US PP33,930 P2
(45) Date of Patent: Feb. 1, 2022

(54) ***COREOPSIS* PLANT NAMED 'RIDING HOOD'**

(50) Latin Name: ***Coreopsis* hybrid**
Varietal Denomination: Riding Hood

(71) Applicant: Darrell Probst, Hubbardston, MA (US)

(72) Inventor: Darrell Probst, Hubbardston, MA (US)

( * ) Notice: Subject to any disclaimer, the term of this patent is extended or adjusted under 35 U.S.C. 154(b) by 0 days.

(21) Appl. No.: 17/356,683

(22) Filed: Jun. 24, 2021

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./417
See application file for complete search history.

*Primary Examiner* — Susan McCormick Ewoldt
(74) *Attorney, Agent, or Firm* — Penny J. Aguirre

(57) ABSTRACT

A new cultivar of hybrid *Coreopsis* plant named 'Riding Hood' that is characterized by its compact plant habit reaching an average of 35 cm in height and 60 cm in width, its floriferous and long blooming season with its nearly sterile inflorescences that do not require deadheading; bloom commences in late-June and lasts until frost in Kensington, Conn., its medium sized inflorescences with ray florets that are dark red in color, its resistance to powdery mildew and leafspot and its cold hardiness at least to U.S.D.A. Zone 4.

2 Drawing Sheets

Botanical classification: *Coreopsis* hybrid.
Variety denomination: 'Riding Hood'.

BACKGROUND OF THE INVENTION

The present invention relates to a new and distinct cultivar of *Coreopsis* plant, botanically of hybrid origin and known as *Coreopsis* 'Riding Hood' and will be referred to hereinafter by its cultivar name, 'Riding Hood'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardiness to at least U.S.D.A. Zone 4 in a wide range of flower colors and plant forms.

The Inventor made a controlled cross in August of 2015 in New Braintree, Mass. between an unnamed and unpatented proprietary plant from his breeding program as the female parent (ref. code N2 14-18) and pollen that was pooled from a variety of unnamed and unpatented proprietary plants from his breeding program as the male parent. The exact pollen parent are therefore unknown. 'Riding Hood' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'Riding Hood' as a unique cultivar of *Coreopsis*.

1. 'Riding Hood' exhibits a compact plant habit reaching an average of 35 cm in height and 60 cm in width.
2. 'Riding Hood' exhibits a floriferous and long blooming season with its nearly sterile inflorescences that do not require deadheading; bloom commences in late-June and lasts until frost in Kensington, Conn.
3. 'Riding Hood' exhibits medium sized inflorescences with ray florets that are dark red in color.
4. 'Riding Hood' exhibits resistance to powdery mildew and leafspot.
5. 'Riding Hood' exhibits cold hardiness at least to U.S.D.A. Zone 4.

The female parent of 'Riding Hood' differs from 'Riding Hood' in having inflorescences with ray florets that are pink in color and in being very fertile causing flower production to stop once seed has set. 'Riding Hood' can be most closely compared to *Coreopsis* cultivars 'Mercury Rising' (U.S. Plant Pat. No. 24,689) and 'Red Elf' (U.S. Plant Pat. No. 27,918). 'Mercury Rising' is similar to 'Riding Hood' in having inflorescences with ray florets that are red in color, resistance to powdery mildew and leaf spot, and in having a long bloom season that does not require deadheading. 'Mercury Rising' differs from 'Riding Hood' in having a taller and wider plant habit and in being hardy to U.S.D.A. Zone 5. 'Red Elf' is similar to 'Riding Hood' in having inflorescences with ray florets that are red in color, a compact plant habit, resistance to powdery mildew and leaf spot, and in having a long blooming season that does not require deadheading. 'Red Elf' differs from 'Riding Hood' in having a more compact and upright plant habit, and in being hardy to U.S.D.A. Zone 5.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on websites by Prides Corner, Proven Winners, EstaBrooksOnline, Grown by Overdevest, Cat Skill Native Nursery, Green River Services Inc, Andrews Greenhouse, Acorn Farms, and Skagit Hort.

BRIEF DESCRIPTION OF THE DRAWINGS

The accompanying colored photographs illustrate the overall appearance and distinct characteristics of the new *Coreopsis*. The photographs were taken of a 4-month-old plant of 'Riding Hood' as grown outdoors in a 1-gallon container in Belchertown, Mass.

The photograph in FIG. 1 provides a view of a plant of 'Riding Hood' in bloom.

Figure 1:
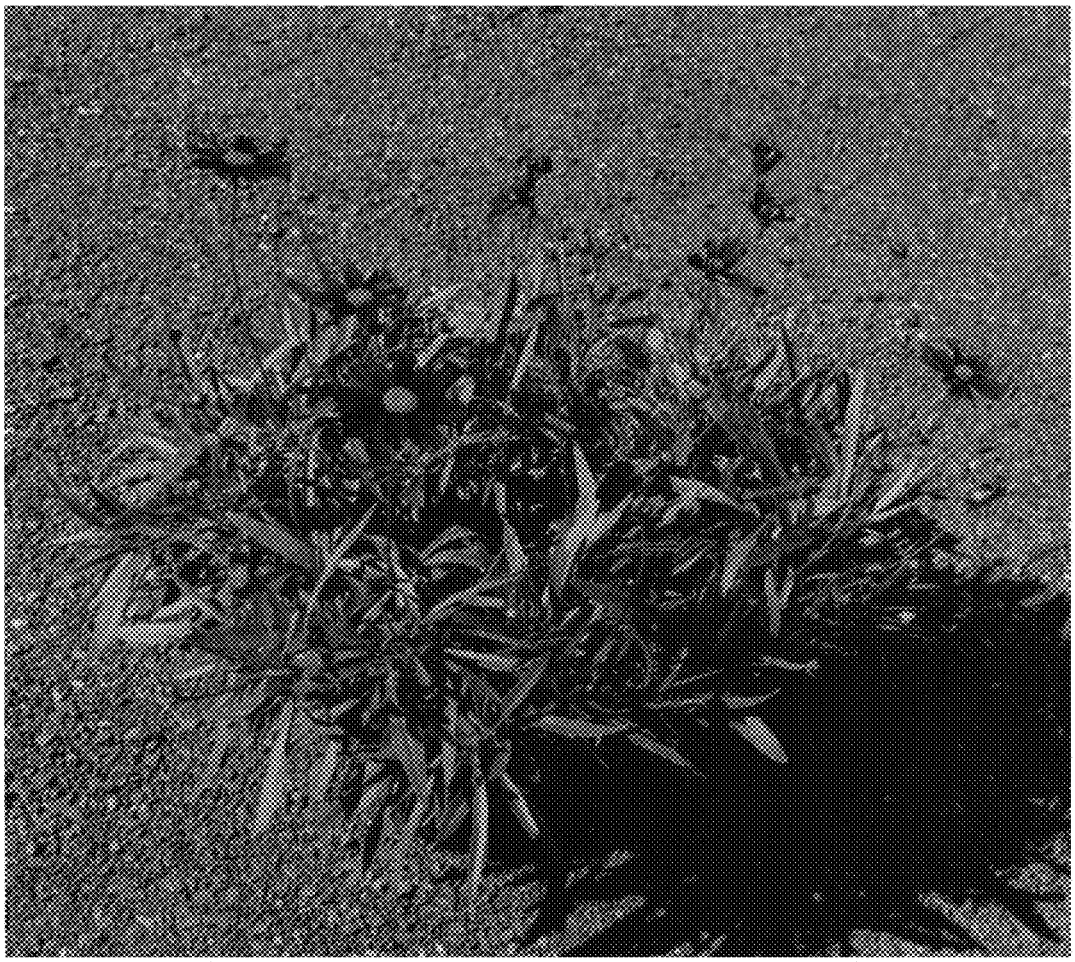
Figure 2:
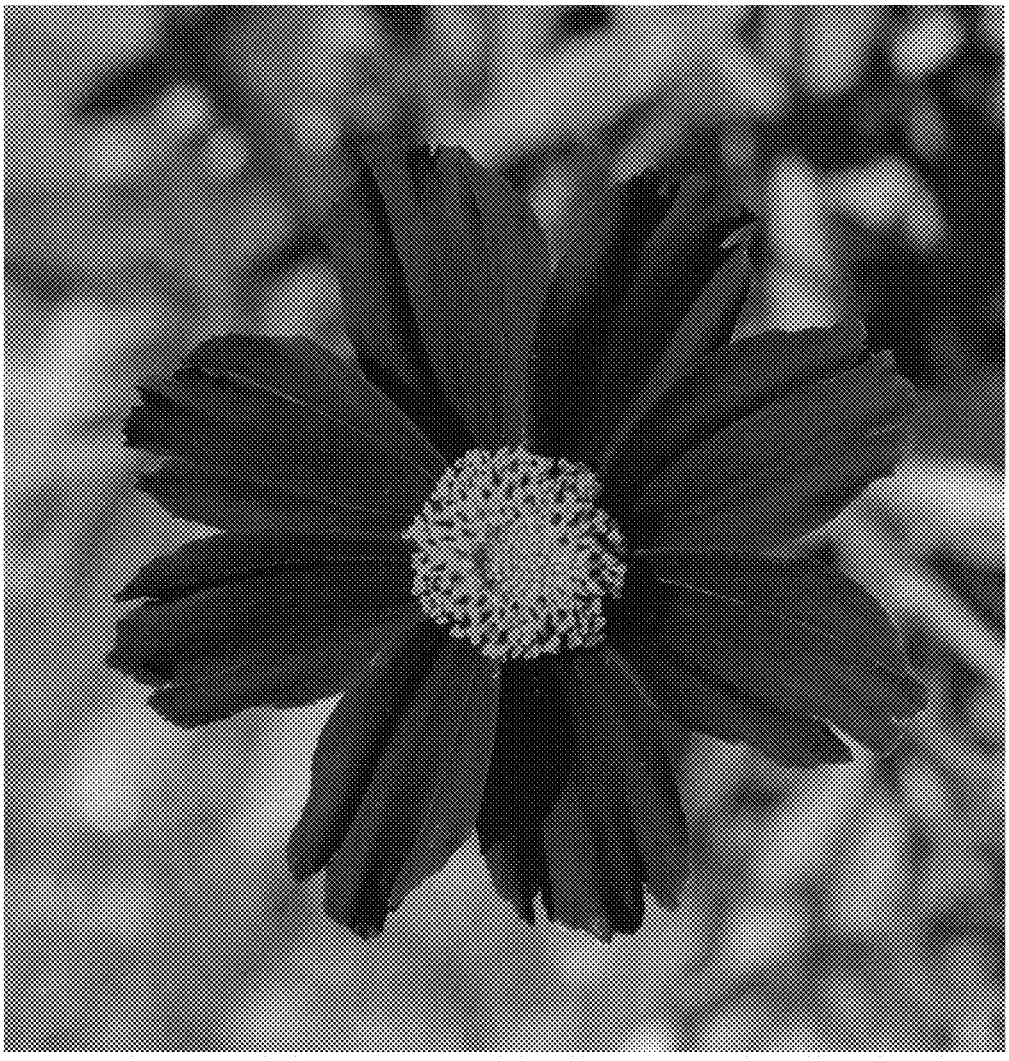

The photograph in FIG. 2 provides a close-up view of an inflorescence of 'Riding Hood'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 4-month-old plants of 'Riding Hood' as grown outdoors in one-gallon containers in Belchertown, Mass. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from late-June until frost in Kensington, Conn.

*Plant type*.—Herbaceous perennial.

*Plant habit*.—Clump-forming, compact, upright leafy flowering stems with inflorescences held above the foliage.

*Height and spread*.—An average of 16 cm in height (foliar plane), 27 cm in height (floral plane) as grown in a one-gallon container, a fully mature plant in the lanscape reaches 35 cm in height and 60 cm in width.

*Cold hardiness*.—At least to U.S.D.A Zone 4.

*Diseases and pests*.—Resistance to powdery mildew (*Podosphaera macularis*) and leafspot (*Pseudomonas cichorii*), no resistance or susceptibility to pests has been observed.

*Root description*.—Fibrous and fine, NN155A in color.

*Propagation*.—Stem cuttings.

*Time required for root initiation*.—An average of 10 days for root initiation.

*Growth rate*.—Vigorous, but stays compact.

Stem description:

*Shape*.—Flattened, solid.

*Stem color*.—144A.

*Stem strength*.—Strong.

*Stem size*.—Main stems; an average of 14 cm in length and 5 mm in width, lateral stems; an average of 6 cm in length (excluding peduncles) and 3 mm in width.

Stem surface.—Glossy, moderately covered with villous hairs up to 2 mm in length and NN155C in color.

*Branching habit*.—Freely branched, an average of 25 basal main stems, lateral stems typically branched as oppositely arranged pairs at each node.

*Internode length*.—An average of 3.5 cm.

Foliage description:

*Leaf division*.—Simple.

*Leaf margins*.—Entire, bi-fid and trifid.

*Leaf size*.—Entire leaves; an average of 9 cm in length and 7 cm in width, trifid leaves; center lobe an average of 7 cm in length and 1 cm in width, lateral lobes an average of 4.5 cm in length and in 5 mm width.

*Leaf shape*.—Linear.

*Leaf base*.—Cuneate.

*Leaf apex*.—Acute.

*Leaf venation*.—Pinnate, inconspicuous, same color as leaf.

*Leaf attachment*.—Sessile.

*Leaf arrangement*.—Opposite.

*Leaf surface*.—Upper and lower surfaces; dull and sparsely to moderately covered with villous hairs; up to 2 mm in length, NN155A in color.

*Leaf color*.—Young and mature upper surface; 138A, lower surface; 138B.

Inflorescence description:

*Inflorescence type*.—Composite with a single row of ray florets surrounding disc florets in the center, forming a radiant head, inflorescences are borne on branch terminals in loose corymbs.

*Lastingness of inflorescence*.—8 to 10 days until senescence of ray florets, phyllarys and disc florets are persistent.

*Fragrance*.—Moderate floral scent.

*Quantity of inflorescences*.—Free flowering, an average of 8 corymbs per main branch, an average of 4 composits per corymb.

*Inflorescence size*.—Corymbs; up to 20 cm in length and 14 cm in width, composite; an average of 2 cm in depth and 6 cm in diameter.

*Inflorescence buds*.—Globose and flattened in shape, an average of 6 mm in depth and 7 mm in diameter, smooth and shiny surface; color; a blend of 146A and 147A.

*Peduncle*.—Rounded in shape, strong, an average of 16 cm in length and 1.5 mm in diameter, 144A in color, smooth and glabrous surface.

Phyllaries (involucral bracts):

*Phyllary number*.—2 rows; outer (lower) row 8, inner (upper) row 8.

*Phyllary arrangement*.—Outer (lower) phyllaries; 5% fused, held horizontal to slightly downwards, inner (upper) phyllaries; surround receptacle with 5% of apical portion free.

*Phyllary size*.—Outer (lower) phyllaries; an average of 1 cm in length and 2 mm in width, inner (upper) phyllaries; an average of 1 cm in length and 5 mm in width.

*Phyllary color*.—Upper and lower surfaces, outer (lower) phyllaries; 144A, base 144B, inner (upper) phyllaries; transluscent, 152B, margins flushed with 22A, base 144A.

*Phyllary texture*.—Outer (lower) phyllaries; glabrous and smooth on both surfaces, inner (upper) phyllaries; glabrous, slightly transluscent and slightly waxy on both surfaces.

*Phyllary apex*.—Acute.

*Phyllary base*.—Truncate.

*Phyllary shape*.—Outer (lower) phyllaries; elliptic to lanceolate, inner (upper) phyllaries; broadly lanceolate.

Ray florets (sterile):

*Number*.—8.

*Shape*.—Oblanceolate, with the appearance of 3 longitudinal sections.

*Size*.—An average of 2.5 cm in length and 1.5 cm in width.

*Apex*.—Rounded with notched and undulate lobes.

*Base*.—Cuneate.

*Margins*.—Entire and slightly undulate.

*Aspect*.—Held mainly horizontal and slightly upwards, perpendicular to peduncle.

*Texture*.—Upper surface; satiny, velvety, glabrous and dull, lower surface; glabrous with a slight sheen.

*Color*.—Upper surface when opening and fully open; closest to a blend of 187A and 187B, lower surface when opening and fully open; 162A with streaks in the mid-section of 187C, margins surrounding the florets 187C.

Disc florets (male and female):

*Number*.—An average of 80.

*Shape*.—Tubular, corolla is fused, flared and slightly curled at apex.

*Size*.—About 5.5 mm in length and 0.4 mm in width.

*Color*.—En masse; 17A, individual; corolla (tube) base and mid-section transluscent, 22A in color.

*Receptacle*.—An average of 1 cm in diameter and 5 mm in depth, 144A in color.

Reproductive organs:

*Presence*.—Disc florets only.

*Gynoecium*.—1 Pistil; an average of 5 mm in length, style; very fine and 8D in color, bifid pillose, stigma; 17B in color with recurved branches about 0.5 mm in length, ovary is inferior, oblong in shape, an average of 2 mm in length and 1 mm in width, and 145A in color.

*Androecium*.—4 stamens, fused into tube surrounding style, an average of 2 mm in length and less than 0.5 mm in width, 200B in color, pollen; abundant in quantity and 22A in color.

*Seed*.—Observed to be nearly sterile, seed development has not been observed to date.

It is claimed:

1. A new and distinct cultivar of *Coreopsis* plant named 'Riding Hood' as herein illustrated and described.

* * * * *